United States Patent
Vayser et al.

(10) Patent No.: US 9,999,345 B2
(45) Date of Patent: Jun. 19, 2018

(54) DROP IN SURGICAL ILLUMINATOR

(71) Applicant: Invuity, Inc., San Francisco, CA (US)

(72) Inventors: Alex Vayser, Mission Viejo, CA (US); Douglas Rimer, Los Altos Hills, CA (US); David Wayne, Watsonville, CA (US)

(73) Assignee: INVUITY, INC., San Francisco, CA (US)

( * ) Notice: Subject to any disclaimer, the term of this patent is extended or adjusted under 35 U.S.C. 154(b) by 0 days. days.

(21) Appl. No.: 14/607,501

(22) Filed: Jan. 28, 2015

(65) Prior Publication Data

US 2016/0008088 A1    Jan. 14, 2016

Related U.S. Application Data

(60) Provisional application No. 61/932,652, filed on Jan. 28, 2014.

(51) Int. Cl.
*A61B 1/32* (2006.01)
*A61B 1/06* (2006.01)
(Continued)

(52) U.S. Cl.
CPC .......... *A61B 1/0684* (2013.01); *A61B 1/07* (2013.01); *A61B 1/128* (2013.01); *A61B 1/3132* (2013.01);
(Continued)

(58) Field of Classification Search
CPC ...... A61B 17/02–17/0293; A61B 90/30–90/37
See application file for complete search history.

(56) References Cited

U.S. PATENT DOCUMENTS 3,070,088 A    12/1962  Brahos
4,738,248 A     4/1988  Ray
(Continued)

FOREIGN PATENT DOCUMENTS

DE    102012110143 A1    4/2014
WO    WO-0015116 A1      3/2000

OTHER PUBLICATIONS

Insightra Medical. Let's Look at Ree Trakt in More Detail. Available at http://www.reetrakt.com/reetrakt/product_details.html. Accessed on Jan. 28, 2015.
(Continued)

*Primary Examiner* — Jan Christopher Merene
*Assistant Examiner* — Steven Cotroneo
(74) *Attorney, Agent, or Firm* — Wilson Sonsini Goodrich & Rosati; Jonathan Feuchtwang

(57) ABSTRACT

An illumination system for adjustably positioning an illuminator in a surgical field in a patient includes an anchor element and an illumination element. The anchor element is configured to be releasably coupled with the patient, and the illumination element is coupled to the anchor element. The anchor element or the illumination element is configured to be coupled, uncoupled, and recoupled with the patient or adjacent surgical equipment. This allows repositioning of the illumination element at a plurality of positions in the surgical field without interfering with adjacent surgical instruments, and further permits adjustment of illumination in the surgical field.

16 Claims, 12 Drawing Sheets

(51) Int. Cl.
  *A61B 17/02* (2006.01)
  *A61B 1/07* (2006.01)
  *A61B 1/12* (2006.01)
  *A61B 1/313* (2006.01)
  *A61B 90/57* (2016.01)
  *A61B 90/30* (2016.01)
  *A61B 17/00* (2006.01)

(52) U.S. Cl.
  CPC .......... *A61B 17/02* (2013.01); *A61B 17/0218* (2013.01); *A61B 90/30* (2016.02); *A61B 90/57* (2016.02); *A61B 17/0206* (2013.01); *A61B 2017/00283* (2013.01); *A61B 2017/00477* (2013.01); *A61B 2017/00876* (2013.01); *A61B 2017/00951* (2013.01); *A61B 2017/0287* (2013.01); *A61B 2090/306* (2016.02); *A61B 2090/309* (2016.02); *A61B 2217/005* (2013.01); *A61B 2218/008* (2013.01)

(56) References Cited

U.S. PATENT DOCUMENTS

| | | | | |
|---|---|---|---|---|
| 5,503,617 A * | 4/1996 | Jako | ................. | A61B 17/02 128/850 |
| 5,569,254 A * | 10/1996 | Carlson | ............. | A61B 17/1644 600/101 |
| 5,588,952 A * | 12/1996 | Dandolu | ............... | A61M 1/008 362/572 |
| 5,967,971 A * | 10/1999 | Bolser | .................... | A61B 17/02 600/211 |
| 5,967,973 A * | 10/1999 | Sherts | ................ | A61B 17/0293 600/205 |
| 6,113,536 A | 9/2000 | Aboul-Hosn et al. | | |
| 6,572,541 B1 | 6/2003 | Petersvik | | |
| 7,022,069 B1 | 4/2006 | Masson et al. | | |
| 8,262,567 B2 * | 9/2012 | Sharp | .................... | A61B 17/02 600/206 |
| 8,317,693 B2 | 11/2012 | Grey et al. | | |
| D673,677 S | 1/2013 | Noda et al. | | |
| 8,343,232 B2 | 1/2013 | Adzich et al. | | |
| 8,551,183 B2 | 10/2013 | Amato et al. | | |
| 8,556,988 B2 | 10/2013 | Amato et al. | | |
| 2001/0029393 A1 | 10/2001 | Tierney et al. | | |
| 2003/0095781 A1 | 5/2003 | Williams | | |
| 2003/0149440 A1 * | 8/2003 | Kammerer | ......... | A61B 1/00087 606/151 |
| 2003/0229267 A1 * | 12/2003 | Belson | ............... | A61B 1/00052 600/109 |
| 2004/0186356 A1 * | 9/2004 | O'Malley | ............... | A61B 17/02 600/231 |
| 2005/0043587 A1 * | 2/2005 | Fujimori | ............ | A61B 1/00029 600/160 |
| 2006/0211918 A1 * | 9/2006 | Lieponis | ............... | A61M 1/008 600/182 |
| 2007/0060795 A1 | 3/2007 | Vayser et al. | | |
| 2007/0232864 A1 | 10/2007 | Sharp et al. | | |
| 2007/0238933 A1 | 10/2007 | Alinsod et al. | | |
| 2007/0293729 A1 * | 12/2007 | Grey | .................. | A61B 1/00105 600/212 |
| 2008/0097162 A1 | 4/2008 | Bonadio et al. | | |
| 2008/0108877 A1 | 5/2008 | Bayat | | |
| 2009/0192530 A1 | 7/2009 | Adzich et al. | | |
| 2011/0172494 A1 | 7/2011 | Bass et al. | | |
| 2012/0116172 A1 | 5/2012 | Butler et al. | | |
| 2012/0209301 A1 | 8/2012 | Bell et al. | | |
| 2012/0215237 A1 | 8/2012 | Amato | | |
| 2012/0232334 A1 | 9/2012 | Bell et al. | | |
| 2012/0253362 A1 | 10/2012 | Noda | | |
| 2013/0197313 A1 | 8/2013 | Wan | | |
| 2013/0245650 A1 | 9/2013 | Adzich et al. | | |
| 2013/0267786 A1 | 10/2013 | Vayser et al. | | |
| 2013/0324801 A1 | 12/2013 | Grey et al. | | |

OTHER PUBLICATIONS

International search report and written opinion dated May 7, 2015 for PCT Application No. PCT/US2015/013359.

European search report with written opinion dated Jan. 3, 2017 for EP15743790.

* cited by examiner

DROP IN SURGICAL ILLUMINATOR

CROSS-REFERENCE TO RELATED APPLICATIONS

The present application is a non-provisional of, and claims the benefit of U.S. Provisional Patent Application No. 61/932,652 filed Jan. 28, 2014; the entire contents of which are incorporated herein by reference.

BACKGROUND OF THE INVENTION

1. Field of the Invention

The present application generally relates to medical devices, systems and methods, and more particularly relates to illumination of a surgical opening during a procedure. More specifically, the present application relates to anchoring of an illumination element to the tissue, surgical draping or other adjacent surgical equipment so that the illumination element is easily anchored to tissue or surgical drapes or other adjacent surgical equipment and preferably without requiring attachment to surgical instruments such as retractor blades. This allows the illumination element to be easily positioned and repositioned in the surgical field intra-operatively without basing its location on the position of retractors or other surgical instruments to which illumination is typically attached to.

Current commercial surgical illumination devices for illuminating surgical fields are often limited to devices that attach to retractor blades or retractor frames. Some are permanently attached and some are detachable. However, there are situations when the retractor or frame may not be convenient for attachment of the illumination device thereto. That happens when the retractor or frame is not positioned right over the specific area of interest, or the coupling mechanism between the illumination device and the retractor or frame may be too cumbersome to use. Since the retractor is often moved during the surgical procedure, this can interfere with illumination of the surgical field provided by the illumination device. Moreover, it may be advantageous to have a drop in illuminator that simply anchors to tissue adjacent the wound and that can be easily dropped into the incision for illumination of the surgical field. Such a device is preferably easy to anchor to the patient or adjacent surgical equipment such as surgical drapes, and may be effortlessly positioned and repositioned thereby allowing a surgeon to easily illuminate different parts of the surgical field during a surgical procedure. Thus it would be desirable to provide illumination devices that can be dropped into a surgical field for illumination thereof and easily anchored. Sometimes it is also desirable to anchor the illumination devices without requiring connection to a retractor or retractor frame. At least some of these objectives will be satisfied by the embodiments disclosed in this specification.

2. Description of the Background Art

There are currently several technologies commercially available that use an illuminator as a stand-alone technology to provide illumination without attaching to a surgical instrument. The most common is an illumination device used during a vetrictomy ophthalmology procedure. In these procedures, a small light pipe is inserted through the eye to allow the surgeon to observe the procedure with a microscope.

Another technology commercially available is in the dental space, where an illuminator that drops into the mouth provides lighting for the dentist. The device is not anchored and can easily move around and get in the way. The patient must bite down on the device in order to anchor it and this can be uncomfortable for the patient. For surgical procedures, most other currently available devices are mounted/attached to surgical instruments used during the procedure and that are adjacent the patient. Thus it would be desirable to provide a more versatile illumination device or system that overcomes some of these challenges. At least some of these objectives will be met by the embodiments disclosed herein.

SUMMARY OF THE INVENTION

The present application generally relates to medical devices, systems and methods, and more particularly relates to illumination of a surgical field in a patient. More specifically, the present application relates to anchoring an illumination element to, or adjacent the patient so that the illumination element is easily anchored to the patient or adjacent surgical equipment without requiring anchoring to surrounding surgical instruments that may be difficult to move or anchor to, and the illumination element is easily repositionable in the surgical field.

In a first aspect of the present invention, an illumination system for adjustably positioning an illumination element in a surgical field in a patient comprises an anchor element and an illumination element. The anchor element is configured to be releasably coupled with the patient, and the illumination element is coupled to the anchor element. It is possible for the anchor and illuminator element to be integral and therefore the same part that are inserted or removed together, or they may be separate components. They do not necessarily need to be detachable from one another. The anchor may comprise two anchor elements, one for anchoring in the surgical field, and the other may be for anchoring to the patient away from the incision. The illumination element may be configured to be coupled, uncoupled, and recoupled with the anchor element, thereby allowing repositioning of the illumination element at a plurality of positions in the surgical field without interfering with adjacent surgical instruments. Similarly the anchor element or the illumination element may be configured to be coupled, uncoupled, and recoupled with the patient or adjacent surgical equipment to allow repositioning of the illumination element at a plurality of positions in the surgical field without interfering with adjacent surgical instruments. Repositioning in either case allows adjustment of illumination in the surgical field. In other embodiments, the entire assembly of the illuminator and the anchor may be repositioned.

The illumination element may be configured to be coupled, uncoupled, and recoupled with the anchor element, thereby allowing repositioning of the illumination element at a plurality of positions in the surgical field without interfering with adjacent surgical instruments.

The anchor element may have a first side configured to be releasably coupled to the patient or adjacent surgical equipment. The first side may comprise an adhesive such as adhesive tape that is configured to releasably attach the anchor element to the patient (e.g. skin) or adjacent surgical equipment. The anchor element may be releasably coupled to the illumination element. The anchor element may comprise hook or loop elements, and the illumination element may comprise hook or loop elements for releasably coupling with the hook or loop elements on the anchor element. The anchor element may comprise a clip or a hook for releasable coupling with the patient or releasable coupling with a surgical drape adjacent the patient or coupling with other adjacent surgical equipment. The anchor element or the illumination element may comprise a magnet for releasably coupling with the other of the anchor element or the illumination element. The anchor element may comprise one or more hooks for releasably coupling with the illumination element. The anchor element may form an open loop or closed loop that is configured to at least partially or completely encircle an incision in the patient.

The system may further comprise a surgical retractor having a retractor blade. The anchor element is preferably not attached to the surgical retractor including attachment to the retractor blade. The illumination element may be configured to be disposed on the surgical field without contacting the surgical retractor.

The illumination element may be a fiber optic, a light emitting diode (LED), an organic light emitting diode (OLED), a fiber optic bundle, a waveguide, a non-fiber optic optical waveguide, or any other element used to illuminate. The illumination element may comprise a tissue engagement element such as a hook adjacent a distal end thereof, and the tissue engagement element may be configured to anchor the distal end of the illumination element to tissue in the surgical field. The tissue engagement element, such as a hook or barb, may be fixedly or releasably coupled to the illumination element. Any of the embodiments may also comprise an imaging element for imaging of the surgical field. The imaging element may be coupled to illumination element, the anchor element or any other component of the system such as the rear shield described below. In some embodiments, the system may include only the imaging element and the proximal and distal anchors without the illumination element. In other embodiments, both the illumination element and the imaging element may be included together. The system may also comprise a suction element that is disposed in or on the illumination element, and that allows smoke or other noxious fumes to be evacuated from the surgical field. Similarly, some embodiments may include only the suction element without the illumination element and without the imaging element. In other embodiments the suction element may be combined with the illumination element and/or the imaging element. Preferably, either embodiment also includes the proximal and distal anchors.

In another aspect of the present invention, a method for illuminating a surgical field in a patient comprises providing an anchor element and an illumination element, wherein the illumination element is coupled to the anchor element, and releasably attaching the anchor element to the patient or adjacent surgical equipment at a first position. The method also comprises uncoupling the illumination element from the patient or adjacent surgical equipment and moving the illumination element to a second position different than the first position. Recoupling the illumination element to the patient or the adjacent surgical equipment allows illumination of a new region of the surgical field.

The step of releasably attaching the anchor element to the patient may comprise adhesively coupling the anchor element to skin on the patient, or otherwise coupling the anchor element to the patient or to the adjacent surgical equipment. Adhesively coupling may comprise taping the anchor element to the patient or the adjacent surgical equipment. The adjacent surgical equipment may comprise a surgical drape disposed over the patient. Releasably attaching the anchor element to the patient may comprise coupling the anchor element to a surgical drape disposed over the patient. Releasably attaching the anchor element may comprise clipping or hooking the anchor element to the patient or clipping or hooking the anchor element to a surgical drape disposed over the patient or to other adjacent surgical equipment. The method may further comprise releasably coupling the illumination element to the anchor element. Releasably coupling the illumination element to the anchor element may comprise coupling the illumination element to the anchor element with hook and loop fasteners. Releasably coupling the illumination element to the anchor element may comprise magnetically coupling the illumination element to the anchor element.

Releasably attaching the anchor element may comprise attaching the anchor element to the patient or the adjacent surgical equipment such that the anchor element forms an open or closed loop that partially or completely encircles an incision in the patient. The illumination element may be coupled to the anchor element without engaging other surgical instruments in the surgical field. The illumination element may comprise a tissue engagement element adjacent a distal end thereof and the method may further comprise anchoring the distal end of the illumination element in the surgical field by engaging the tissue engagement element with tissue in the surgical field. The tissue engagement element may be releasably coupled to the illumination element. The method may further comprise the steps of anchoring a distal end of the illumination element in the surgical field, applying a tension to the illumination element, anchoring a proximal end of the illumination element to the patient or the adjacent surgical equipment, and maintaining the tension.

In some embodiments, the illumination element or the tissue engagement element may include extended flanges or wings. These wings may be then be pinned against the tissue by a retractor blade or other surgical instrument in order to secure the distal portion of the illumination system and prevent unwanted movement. In still other embodiments, the method may further comprise imaging the surgical field with an imaging element that may be coupled to the illumination element or provided without the illumination element, or coupled to the anchor element or any other component of the system such as a rear shield described below. The method may also comprise evacuating smoke or other noxious fumes from the surgical field.

In still another aspect of the present invention, an illumination system for adjustably positioning an illuminator in a surgical field in a patient comprises a rear shield having a proximal portion and a distal portion, an anchor element coupled to the rear shield adjacent the proximal portion thereof, wherein the anchor element is configured to be attached to the patient or adjacent surgical equipment, and an illumination element that is configured to illuminate a surgical field.

The system may further comprise a tissue anchor element adjacent the distal portion of the rear shield and that is configured to engage tissue in the surgical field. The tissue anchor element may be releasably coupled to the distal portion of the rear shield. The anchor element may comprise a strap that is adjustably coupled to the proximal portion of the rear shield. The strap may be configured to be releasably coupled to the patient or the adjacent surgical equipment. The strap may be fixedly coupled to the rear shield or it may be releasably coupled thereto. The distal portion may comprise a pair of wings forming an open channel and the illumination element may be disposed in the channel. The strap may comprise a portion with an adhesive region for adhesively coupling the strap with the patient or the adjacent surgical equipment, or the strap may comprise a hook and loop fastener region for coupling the strap with the patient or the adjacent surgical equipment. The distal portion of the strap may overlap with itself to form an overlapping region that is coupled to itself with hook and loop fasteners. The strap in the overlapping region may be releasably coupled to itself, or it may be fixedly coupled to itself. The system may further comprise a ramp element disposed near the proximal portion, and the ramp element may be configured to prevent cantilevering of the rear shield outward and away from the surgical field when traction is applied thereto. The strap may be coupled to a proximal-most end of the rear shield. The strap may have a region with an adhesive for coupling the strap with the patient. The system may comprise a pad coupled to the patient or the adjacent surgical equipment that is also coupled to the strap or the rear shield. Still other embodiments may further comprise an imaging element that is coupled to the illumination element, the anchor element or any other component of the system such as a rear shield described elsewhere in this specification. The imaging element is configured to provide an image of the surgical field. The system may also comprise a suction element for removing smoke or other noxious fumes from the surgical field. The suction element may be disposed on or in the illumination element or the rear shield. As disclosed previously, the system may include only the illumination element, only the imaging element or only the suction element. In still other embodiments, the system may include any combination of one or more of the illumination element, imaging element or suction element.

The system may comprise a heat sink that is thermally coupled to the rear shield. The rear shield may be polished or have a lightened surface in order to reduce heat absorption of the rear shield. The rear shield may comprise a layer of plating to increase the thermal conductivity of the rear shield. The system may further comprise an insulating thermal barrier such as fluorinated ethylene propylene, which is disposed between the rear shield and the illumination element.

In yet another aspect of the present invention, a method of illuminating a surgical field in a patient comprises providing a rear shield. The method also includes anchoring a proximal portion of the rear shield to the patient or to surgical equipment adjacent the patient, and coupling an illumination element to the rear shield. The surgical field is illuminated with light from the illumination element.

The method may further comprise applying a tension to the rear shield. The method may also comprise anchoring a distal portion of the rear shield to tissue in the surgical field. Anchoring the distal portion may comprise engaging an anchor element with the tissue, and anchoring the proximal portion may comprise coupling a strap to the proximal portion of the rear shield. Anchoring the proximal portion may comprise adhesively coupling the strap with the patient or with the surgical equipment. Anchoring the proximal portion may comprise releasably coupling the strap with the patient or with the surgical equipment by using hook and loop fasteners, clipping, or magnetic coupling. The method may also comprise anchoring the proximal portion by coupling the strap to a pad that is coupled to the patient or the adjacent surgical equipment. Anchoring the proximal portion may comprise coupling the proximal portion to a pad that is coupled to the patient or the adjacent surgical equipment.

The method may further comprise adjusting length or tension in the strap. The method may also further comprise unanchoring the rear shield, repositioning the rear shield to a new position in the surgical field, re-anchoring the rear shield in the surgical field, and illuminating the new position with light from the illumination element. The method may also comprise imaging the surgical field with an imaging element that may be coupled with the anchor element, the illumination element, or any other component of the system such as a rear shield.

The method may further comprise removing heat from the rear shield with a heat sink or removing heat from the rear shield and maintaining peak temperature of the rear shield or the illumination element below 41° C. The rear shield may be polished or have a lightened surface in order to reduce absorption of heat by the rear shield. The thermal conductivity of the rear shield may be increased by providing a layer of plating on the rear shield. The method may also comprise insulating heat from the rear shield by providing a thermal insulating barrier disposed between the rear shield and the illumination element.

In yet another aspect of the present invention, a method for imaging a surgical field in a patient comprises providing an anchor element or a rear shield and coupling an imaging element to the anchor element or the rear shield. The anchor element or the rear shield may be anchored to the patient or to adjacent surgical equipment and the imaging element may be used to provide an image of the surgical field. The method may also comprise evacuating smoke or other noxious fumes from the surgical field with or without illumination and with or without imaging.

In another aspect of the present invention, an illumination system for adjustably positioning a surgical tool in a surgical field in a patient comprises a rear shield and an anchor element. The rear shield has a proximal portion and a distal portion and also has a coupling mechanism configured to be releasably coupled to the surgical tool. The anchor element is coupled to the rear shield adjacent the proximal portion thereof, and the anchor element is configured to be attached to the patient or adjacent surgical equipment.

The system may further comprise a tissue anchor element that is adjacent the distal portion of the rear shield. The tissue anchor element may be configured to engage tissue in the surgical field and may be releasably coupled to the distal portion of the rear shield. The anchor element may comprise a strap that is adjustably coupled to the proximal portion of the rear shield. The strap may be configured to releasably coupled to the patient or to adjacent surgical equipment. The strap may be fixedly coupled to the rear shield.

The distal portion of the rear shield may comprise a pair of wings that form an open channel sized to receive the surgical tool. The surgical tool may comprise an illumination element or an imaging element.

The system may further comprise a ramp element that is disposed near the proximal portion of the rear shield. The ramp element may be configured to prevent cantilevering of the rear shield outward and away from the surgical field when traction is applied thereto. The strap may be coupled to a proximal-most end of the rear shield. The strap may comprise a region with an adhesive for coupling the strap with the patient, or the strap may comprise a region with hook and loop fasteners for coupling the strap with the patient or the adjacent surgical equipment. A distal portion of the strap may overlap with itself to form an overlapping region, and the overlapping region may be releasably coupled to itself or fixedly coupled to itself. The system may further comprise a pad that is coupled to the patient or the adjacent surgical equipment. The pad may also be coupled to the strap or the rear shield.

The system may further comprise an imaging element that is coupled to the rear shield or the surgical tool. The imaging element may be configured to provide an image of the surgical field. The system may comprise a suction element on or in the rear shield or the surgical tool. The suction element may be a tube, channel or other structure which is configured to remove smoke or noxious fumes from the surgical field. The system may further comprise a heat sink that is thermally coupled to the rear shield. The rear shield may have a polished or lightened surface to reduce absorption of heat by the rear shield. The rear shield may have a layer of plating to increase its thermal conductivity. An insulating thermal barrier such as fluroinated ethylene propylene (FEP) may be disposed between the rear shield and the surgical tool. Any one or more of the imaging element, illumination element or suction element may be integral with the proximal or distal anchors and therefore be a single component.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Specific embodiments of the disclosed device, delivery system, and method will now be described with reference to the drawings. Nothing in this detailed description is intended to imply that any particular component, feature, or step is essential to the invention.

Figure 4:
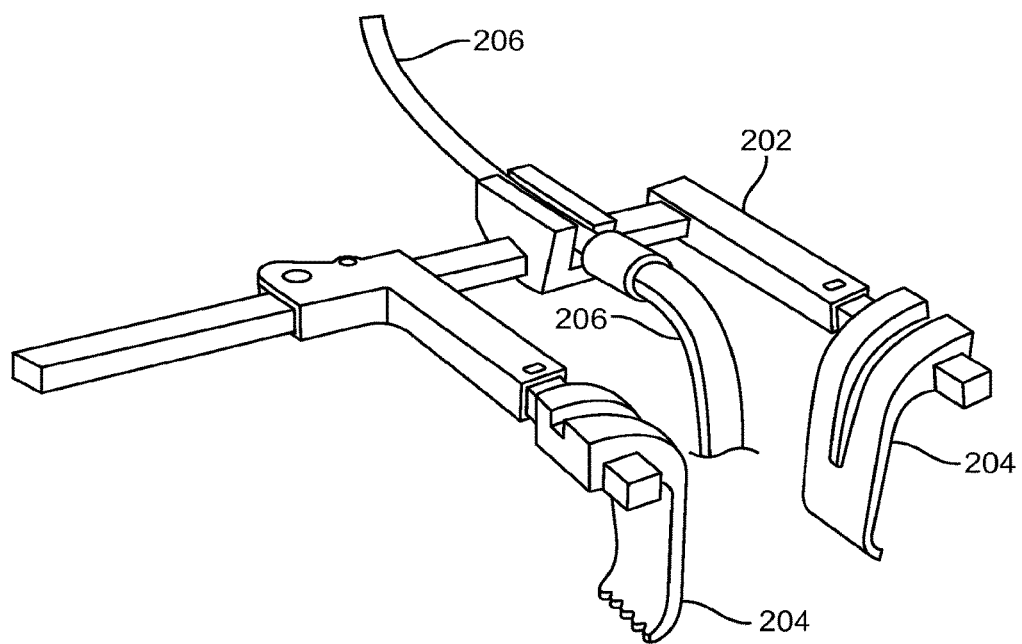
FIG. 4 illustrates an illuminator attached to a surgical retractor frame.

Surgical illuminators are often coupled to a surgical instrument such as a retractor blade or retractor frame. FIG. 4 illustrates the illumination element 206 coupled to a retractor frame 202 having blades 204. An input cable 206 such as a fiber optic cable allows light to be input from an external source to the illumination element 206.

Thus, the surgical illuminator position is fixed relative to the surgical field and this can be inconvenient for a surgeon who may require illumination of the surgical field to be adjusted during surgery, or for the illuminator to be moved to a different position in the surgical field in order to accommodate surgical instruments or a surgeon's hands. Also, the retractors are often moved during surgery and this moves the illuminator as well, and therefore the surgical field may not be illuminated optimally. Therefore, it would be desirable to provide a surgical illuminator that can be anchored adjacent a surgical field independently of some surgical instruments and that can be easily positioned and repositioned without interfering with the other surgical instruments in the area.

Figure 1:
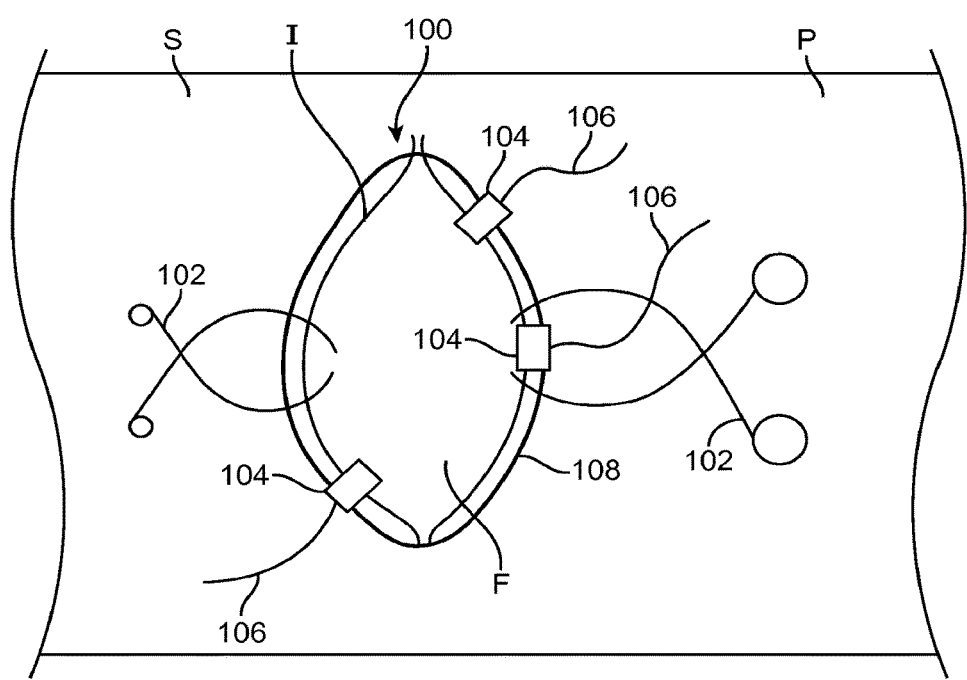
FIG. 1 illustrates a top view of an illuminator in a surgical field.

FIG. 1 illustrates an exemplary embodiment of a drop in illuminator system 100 which includes one or more illumination elements 104 releasably coupled to an anchor element 108. The illuminator system 100 is used to illuminate a surgical field F formed after making an incision I through skin S in a patient P. Surgical instruments such as Gelpi retractors 102 are often disposed in the surgical field F and engage tissue. Optional light input cables 106 such as fiber optic cables couple the illumination elements 104 with external light sources, such as xenon light. The light input cable 106 may be an integral pigtail coupled with the illumination element. In these embodiments, the light input cable may be a single fiber optic cable or a fiber optic bundle that is integrally coupled with a proximal portion of the illumination element. The input cable may be insert molded, over molded or otherwise coupled to the illumination element. In still other embodiments, the integral connection may be formed by placing the input cable into one or more receptacles on a proximal portion of the illumination element and bonding them into position with an adhesive such as epoxy, or an indexing matching adhesive. In still other embodiments the light input may be butt coupled with the proximal portion of the illumination element. In this embodiment, the distal most face of the light input is opposed with a proximal face of the illumination element. The two components may be coupled together with adhesives, index matching adhesives or otherwise coupled together using techniques known in the art, such as with an ACMI standard optical connector.

Because the retractors 102 are often moved during a surgical procedure, it would be desirable to avoid having to anchor the illumination elements to the retractors. Therefore, an anchor element 108 is coupled to the patient and the anchor element is then used to releasably hold the illumination element 104. The illumination element may be attached to the anchor element at one position, and then it may be moved to a second different position and recoupled to the anchor element to illuminate a different portion of the surgical field without coupling with other surgical instruments in the wound or otherwise interfering with the surgical instruments or having to engage them.

In this exemplary embodiment, the anchor element 108 forms a loop around the incision I and at least partially encircles the incision. The loop may be a closed loop or an open loop and thus the anchor element may partially or completely encircle the incision. Thus, the illumination element may be moved circumferentially anywhere around the incision. The anchor element may therefore form a partial or complete circle, ellipse, arc, square, rectangle or other pattern partially or completely around the incision. However, in other embodiments, the anchor element may only be disposed at a single location adjacent the incision or the anchor element may have a plurality of discrete locations around the incision.

Figure 2:
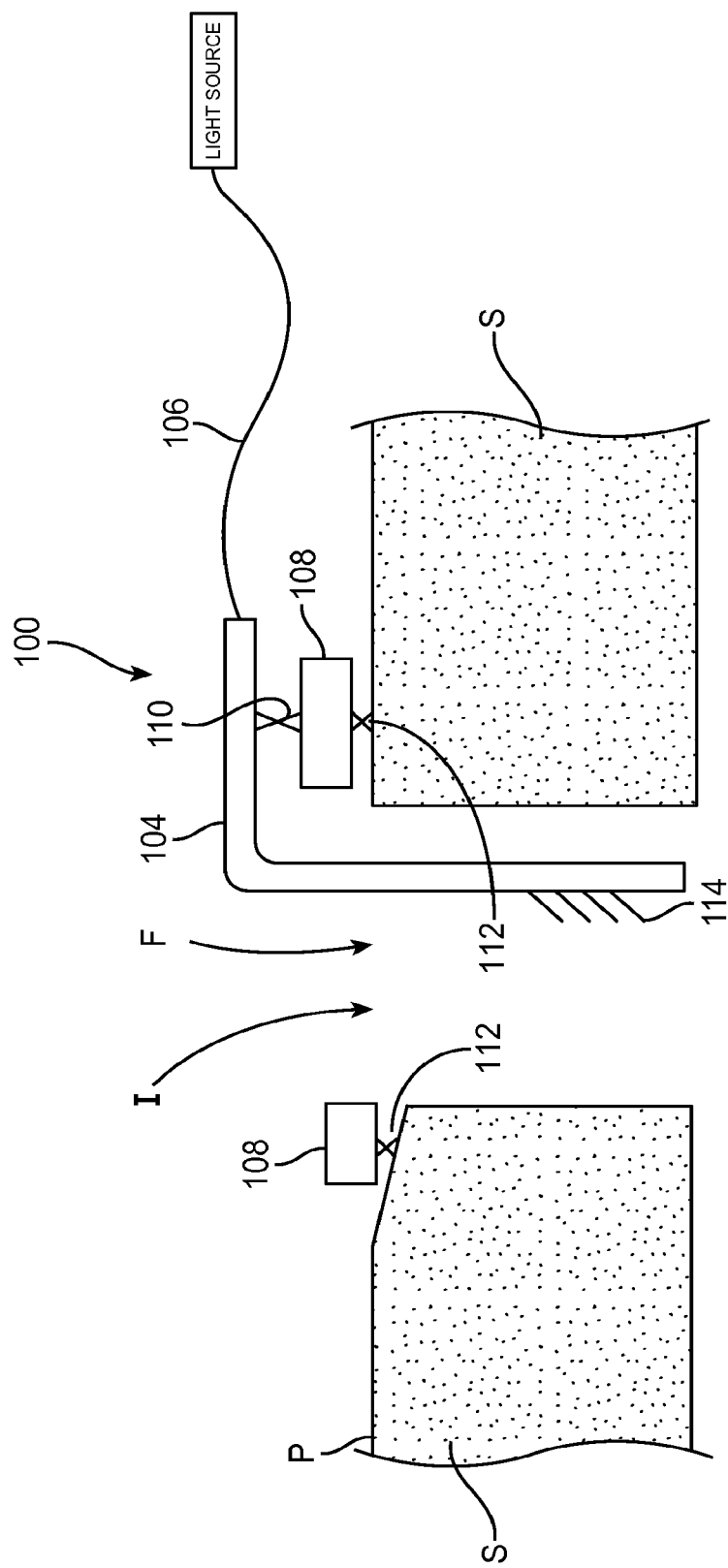
FIG. 2 illustrates a side view of the illuminator in FIG. 1.

FIG. 2 illustrates a side view of the illumination element 104 disposed through the incision I and positioned in the surgical field F. The illumination element 104 is releasably coupled to the anchor element 108 by a connection 110. Similarly the anchor element 108 is releasably coupled to the patient by connection 112. Light 114 emitted from the illumination element 104 illuminates the surgical field F. Additional details on the connections 110 and 112 are disclosed below.

Connection 112 is formed between the anchor element 109 and the patient P. The anchor element 108 may be adhesively coupled to the patient's skin such as with tape disposed between the skin and a backside of the anchor element. The adhesive tape is preferably disposed adjacent a proximal portion of the anchor element. In other embodiments, the anchor element may have a hook or a clip near the proximal end of the anchor element that can attach to the patient's skin or attach to a surgical drape disposed over the patient or that can be coupled to other adjacent surgical equipment. In still other embodiments hook and loop fasteners such as Velcro® may be coupled to the anchor element and used to attach the anchor element to another section of hook and loop fasteners already coupled to the patient, drapes or other surgical equipment in the area. Any of these connection techniques may be used in any of the embodiments disclosed herein.

Connection 110 is formed between the illumination element 104 and the anchor element 108. The connection 110 may be formed with adhesive such as tape, or in other embodiments hook and loop fasteners such as Velcro® may be used to join the anchor element and the illumination element. In some embodiments, the anchor element has adhesive on the bottom surface for attachment to the patient's skin, and hook and loop fasteners on the top surface for coupling with the illumination element. In still other embodiments, connection 110 may be formed with hooks, snap fits, magnets, or other coupling mechanisms known in the art. Any of these connection techniques may be used in any of the embodiments disclosed herein.

In still other embodiments, the anchor is not coupled directly to a patient's skin, but instead the anchor element includes a clip or hook for coupling the anchor element to a surgical drape disposed over the patient. In still other embodiments, the anchor element may be stapled, sutured or otherwise coupled to the patient's skin or surgical equipment in the area such as surgical drapes.

In still other embodiments, a proximal portion of the illumination element includes the anchor element and thus is coupled to the patient. For example, double sided adhesive tape may be applied to an underside of the proximal portion of the illumination element. One surface of the adhesive tape is therefore coupled to the illumination element and the other side of the adhesive tape is coupled to the patient or to adjacent surgical equipment such as a surgical drape. In yet other embodiments, a strap or tether may be coupled to the proximal portion of the illumination element and the strap is then coupled to the patient or adjacent surgical equipment using any of the anchoring techniques described in this specification.

In use the anchor element is releasably coupled to the patient's skin, a surgical drape or other surgical equipment, or otherwise coupled to the patient. The illumination element is then disposed in the wound. The proximal portion of the illumination element is then coupled to the patient or adjacent surgical equipment using any of the above disclosed connections. The illumination element may then be illuminated with an internal light source, or an external light source may be optically coupled to the illumination element. During surgery, the illumination element may be moved to different positions around the incision as required in order to illuminate different portions of the surgical field or to reposition the illumination element if it obstructs the surgical field.

Optionally, tension may be applied to the illumination element by coupling a distal portion of the illumination element to tissue in the surgical field. The proximal portion of the illumination element is then coupled to the patient or adjacent surgical equipment thereby maintaining tension in the illumination element. The tension helps ensure that the illumination element is securely anchored to the patient. The tension may be adjusted to retract tissue or it may be adjusted to a level of tension that does not retract tissue.

Figure 3:
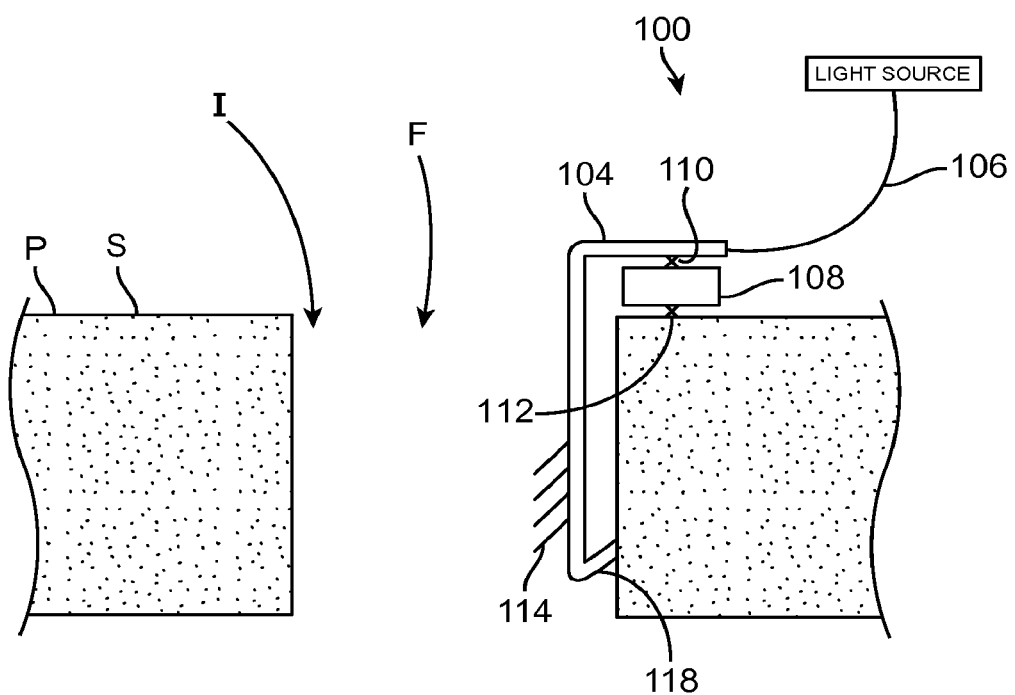
FIG. 3 illustrates a side view of an illuminator engaged with tissue.

FIG. 3 illustrates a side view of the illumination element 104 coupled to anchor element 108 and disposed through the incision I and into the surgical field F. The distal portion of the illumination element may include a hook 118 or barbs or other tissue engagement features for anchoring the distal portion of the illumination element into the tissue. This embodiment generally takes the same form as previous embodiments with the exception of the tissue engagement element such as the hook or barbs. The tissue engagement element may be integral with the illumination element, or it may be releasably coupled thereto.

Figure 5:
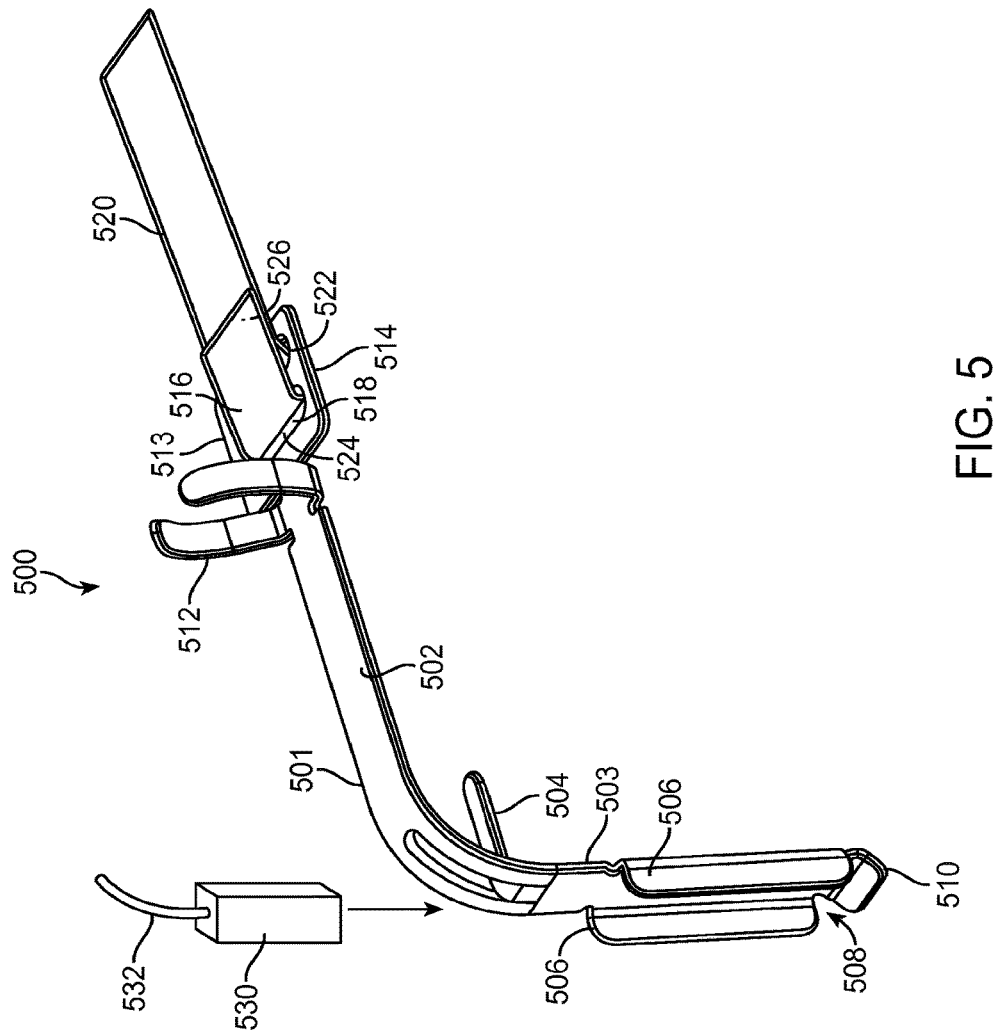
FIG. 5 illustrates an exemplary embodiment of an illuminator rear shield.

FIG. 5 illustrates another exemplary embodiment of a drop in illuminator 500. The illuminator 500 includes a rear shield 501 having a proximal portion 502 and a distal portion 503. The proximal portion includes a generally flat planar section 502 and an attachment section 513. The attachment section allows the rear shield 501 to be coupled to a flexible member such as a strap 520 which is then attached to the patient in any of the ways described above. This includes but is not limited to using adhesive, clips, hooks, or hook and loop fasteners on one side of the strap 520 to couple the strap to the patient, to hook and loop fasteners already coupled to the patient, or to a surgical drape or other surgical equipment adjacent the incision. The strap 520 is preferably flexible and a portion 516 enters a first slot 522, passes under a bar and a portion 524 exits a second slot 518. The leading edge of the strap overlaps 526 a portion of the strap entering the first slot and the two portions of the strap may be fixedly or releasably coupled together with adhesive, hook and loop fasteners, clipped together, stitched together, or otherwise coupled together using techniques known in the art. The attachment may be adjustable so that tension on the rear shield may be adjusted as will be discussed later. In alternative embodiments, the proximal portion of the rear shield may be longer and extend further proximally and this portion may be attached to the patient with hook and loop fastener, adhesive, suture, clips, staples, etc. and thus a strap is not required. In still other embodiments, the proximal portion of the rear shield is releasably coupled to an anchor pad that is attached to the patient using any of the techniques described above. In still other embodiments, the strap may be releasably coupled to a separate anchor pad that is coupled to the patient. This coupling may be formed using any of the coupling mechanisms previously described (e.g. hook and loop, adhesive, clip, hook, etc.) and the anchor pad may be a pad of material which is attached to the patient's skin or adjacent surgical equipment (e.g. a surgical drape). The pad may be adhesively coupled to the patient or adjacent equipment, stapled, sutured, clipped, hooked, or by other techniques known in the art. This or any of the anchor pads disclosed herein may be flexible and may have an area that is disposed entirely on the patient's skin or on a surgical drape, or other adjacent surgical equipment.

A pair of arms 512 on the proximal portion of the rear shield is sized to receive a waveguide illuminator 530, fiber optic cables 532, or other attachments to help secure them in place. The distal portion 503 is generally transverse to the plane in which the proximal portion lies, in this exemplary embodiment the distal portion is substantially orthogonal to the proximal portion. A tab 504 may be formed out of the proximal portion of the rear shield and bent radially outward to serve as an anchor for engaging and anchoring the rear shield in tissue. In alternative embodiments, the tissue anchor may be releasably coupled with the rear shield, or it may be integrally formed therewith. A pair of wings 506 on either side of the distal portion 503 form an open channel 508 in which an illuminator such as a waveguide 530, fiber optic cable 532 or other illumination device may be disposed. The fiber optic input cable 532 may be coupled to a proximal portion of the illuminator 530 using any of the techniques previously described above, and the illumination device may be any of those known in the art, including those disclosed in U.S. Pat. No. 8,317,693, the entire contents of which are incorporated herein by reference. A curved distal tip 510 also helps secure the illuminator in the channel 508 and also provides an atraumatic tip for minimizing or avoiding tissue damage when the rear shield is used. In alternative embodiments, the illumination device may be used in conjunction with, or substituted with any other instrument or device, such as an imaging element like a camera or a suction element for smoke removal. Any combination of these elements is possible.

In use, the rear shield 500 is disposed in a surgical incision with the distal portion 503 extending into the incision. The flat planar proximal portion 501 is generally disposed outside the incision and lies on top of the patient's skin or against a surgical drape. Once the rear shield is positioned, the proximal end may be retracted proximally so that tab 504 engages tissue and prevents the rear shield from moving proximally. The strap 520 is then coupled to the proximal portion of the rear shield by wrapping the strap through the various slots in the attachment section 513. The strap is then coupled to the patient as previously described. The overlapping portion of the strap that is coupled to itself can further be detached and reattached in order to further adjust tension. The proximal and distal portions of the rear shield are now secured and the rear shield is secured in position. An illuminator such as a waveguide, fiber optics, LEDs, OLEDs, or another illumination element may then be dropped in to the rear shield to illuminate the surgical field. The entire assembly may be adjustably positioned around the surgical incision as required in order to provide illumination to various regions of the surgical field as required. In other embodiments, the illumination element may be dropped into the channel and coupled to the rear shield before the rear shield is coupled with the patient.

Figure 6A:
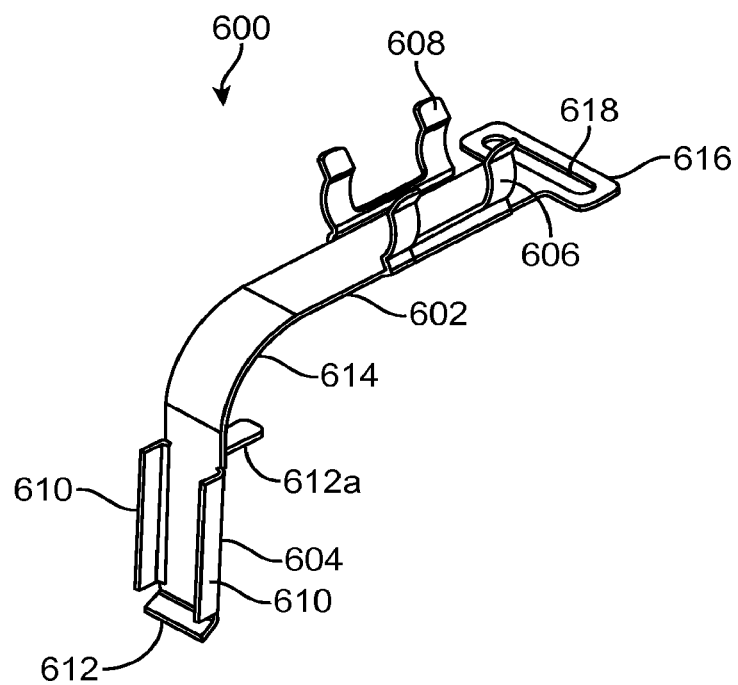
FIGS. 6A-6B illustrate another exemplary embodiment of an illuminator rear shield.
Figure 6B:
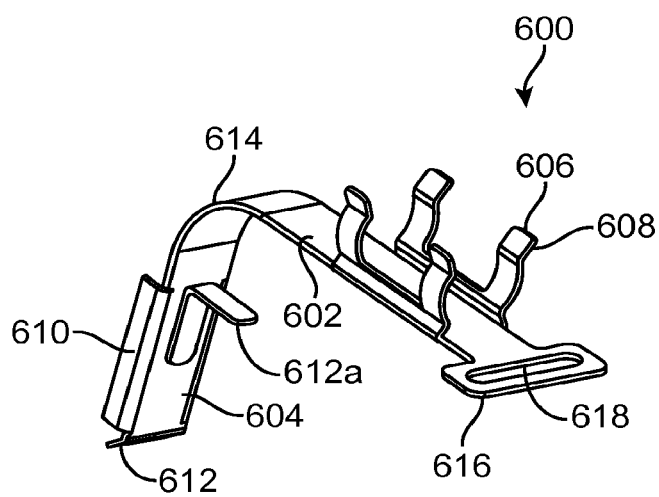

FIGS. 6A-6B illustrate another exemplary embodiment of an illuminator rear shield. The rear shield 600 is similar to the embodiment in FIG. 5 with the major difference being the mechanism for holding the fiber optic input cable and the mechanism for coupling to a strap or other anchor element. Rear shield 600 includes a flat rectangular and planar proximal portion 602 and a flat rectangular planar distal portion 604 that is transverse to the proximal portion 602. In this embodiment, the distal portion 604 is bent at a transition region 614 to be orthogonal to the proximal portion 602. The clip mechanism 606 has four resilient fingers 608 that are biased to return to a relaxed position in order to releasably hold a fiber optic cable, other cables or a waveguide that is inserted in the cradle formed by the fingers 608. This is similar to the previous embodiment except that this embodiment has more fingers. The distal portion 604 also have a pair of wings 610 that extend outward from the distal portion in order to form a channel for receiving the illumination element (not illustrated). A wing 612 on the distal portion also forms a stop to prevent the illumination element or whatever device is coupled therewith (e.g. suction device, imaging element, etc.) from moving distally too far. A tab 612a generally transverse to the proximal portion extends outward and away from the rear shield and serves as a tissue anchor for engaging the rear shield with tissue in the surgical field. The proximal portion of the rear shield also includes an engagement mechanism 616 for coupling the rear shield to another anchor element such as a strap. The engagement mechanism 616 has a single slot 618 transverse to the longitudinal axis of the rear shield that is sized to receive a strap. The strap may enter the slot and exit the slot forming a loop and the strap may then be secured to itself with adhesive, hook and loop fasteners, sewn, sutured, stapled, or otherwise coupled together using techniques known in the art. FIG. 6B illustrates the rear shield 600 from a different angle.

To minimize the risk of burns, ISO standard 60601 requires that the temperature of any tissue contacting surface must be less than 41° C. Light emitted from the rear surface of the waveguide that is absorbed by the near surface of a shield or backing strip generates heat. This heat input results in a temperature increase of the shield. From a safety perspective the peak temperature as opposed to the average temperature is most relevant. So assuming that a high concentration of light energy is absorbed within a relatively focal area of the shield, then two shields of different materials with similar heat capacity will heat up differently based on their material properties. If one shield material is a poor thermal conductor, a local hot spot will occur because the heat will not be readily dissipated away from the focal input, whereas a material that is a good heat conductor dissipates the focal heat much more evenly throughout the mass resulting in a lower peak temperature. This is why pans are made of copper or aluminum, to heat more evenly.

Considering the desire to minimize the size of a surgical incision, the profile of the drop-in illuminator and preferably the rear shield must be as low as possible while maintaining adequate rigidity to retain its shape when retraction force is applied. Alternatively, the surgeon may wish to adjust the shape of a malleable section of rear shield or backing strip. Materials that can be selectively heat treated or annealed to vary rigidity or malleability as desired include aluminum and stainless steel. Steel is approximately three times more rigid than aluminum, so a comparatively thin strip of stainless steel formed into a shield or backing strip will provide an equivalent rigidity. However, aluminum is greater than ten times more thermally conductive than stainless steel, with more than twice the heat capacity of stainless steel, so when focally emitted light is absorbed a higher peak temperature will be present on the tissue contacting surface of the stainless steel shield; depending on the intensity of the light, this temperature may exceed 41° C.

This peak temperature can be reduced by several methods, including: 1) reducing the absorption by polishing or lightening the color of the surface, and/or 2) increasing the thermal conductivity of the shield such as by plating with a high conductivity metal on one or both surfaces to more effectively sink or diffuse the increased heat, potentially in combination with 3) an insulating thermal barrier coating on the tissue contacting surface such as a ceramic coating. Any of these may be used in conjunction with any of embodiments described herein. Therefore, for example a rear shield may have surfaces which are polished or the color is lightened, the heat conductivity of the rear shield may be increased by plating or other techniques, or an insulating thermal barrier may be coupled to the rear shield. Additionally, any combination of these features may also be utilized with the rear shield embodiments or the other illuminator embodiments.

Figure 10A:
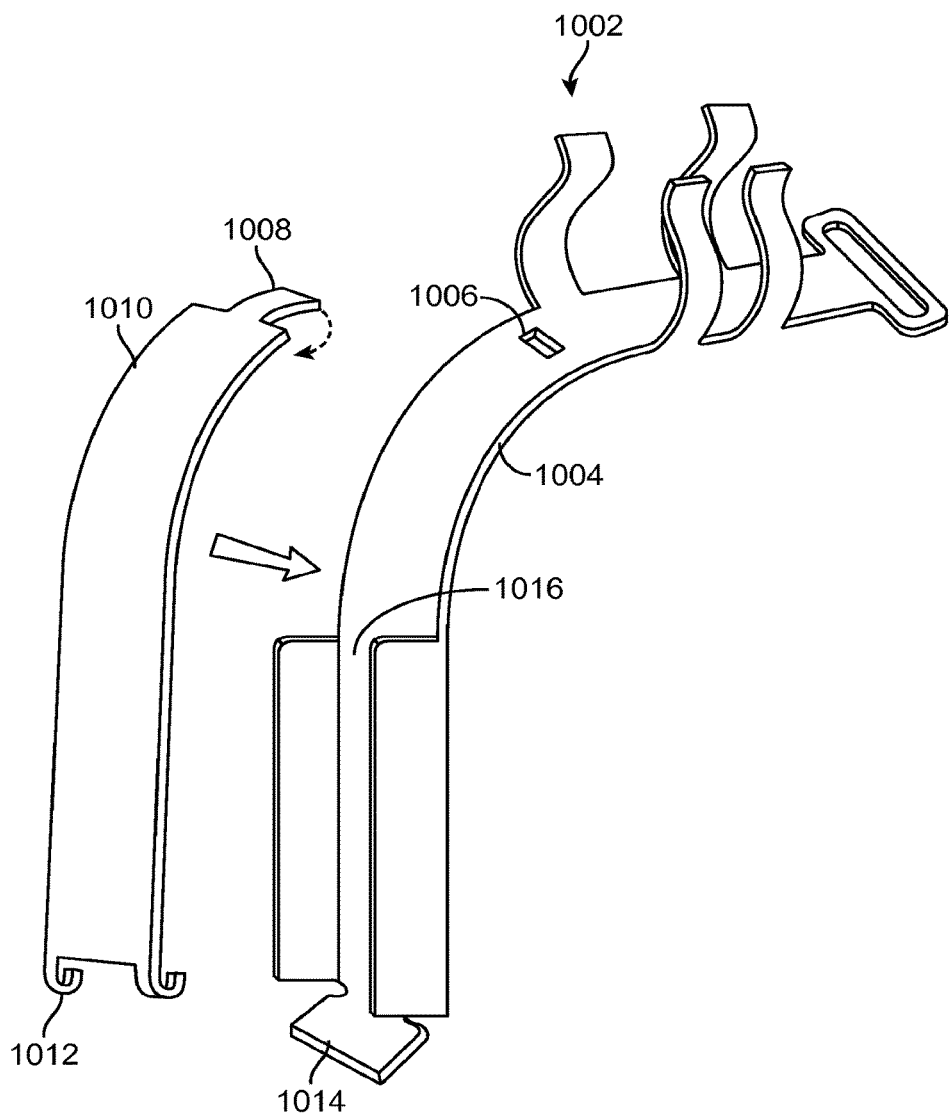
FIGS. 10A-10B illustrate a heat sink used with a rear shield.
Figure 10B:
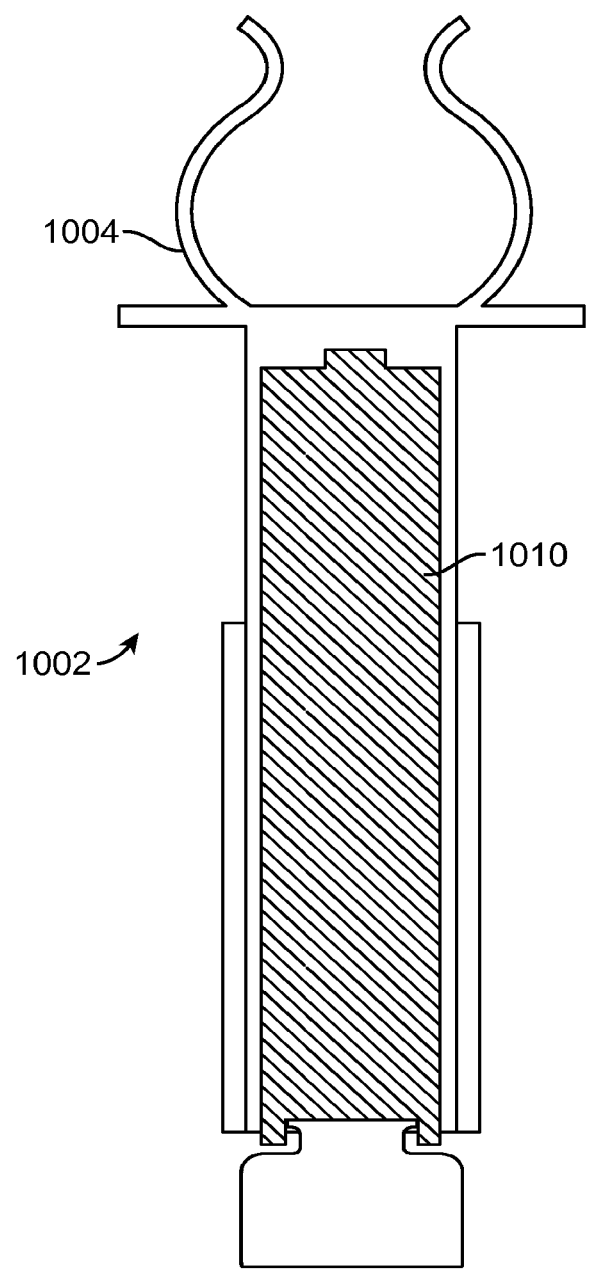

A heat sink may also be used to help manage heat generated by the illuminator. FIGS. 10A-10B illustrate an exemplary embodiment of a rear shield assembly 1002 having a heat sink. FIG. 10A illustrates rear shield 1004 which may be any of the rear shield embodiments described herein and heat sink 1010 having engagement tabs 1008 and 1012. Tabs 1012 may be hooks that are sized and configured to engage a distal portion 1014 of the rear shield 1004. Tab 1008 may be sized to be received in a receptacle 1006 on the rear shield. Tab 1008 may be bent after insertion into receptacle 1006 in order to lock the tab in position, or it may be glued or otherwise attached to the rear shield. The heat sink may be any material suitable for heat removal, such as 6061 aluminum. It may also be anodized black in order to further facilitate with heat management. While any size or thickness may be used, preferably the heat sink has a low profile such as 0.010" to 0.015" thick. The heat sink is preferably sized to fit in channel 1016 in rear shield 1002 and the heat sink conforms to the contour of the rear shield. The rear shield may be any material but preferably is 17-4 stainless steel and may be about 0.005" to 0.0030" thick, and more preferably 0.010" to 0.020" thick, and most preferably has a thickness of about 0.015" thick. Thus the assembly has a thickness preferably about 0.030" to about 0.035" although one of skill in the art will appreciate that other dimension are possible. FIG. 10B illustrates a front view of the assembly 1002.

Figure 11:
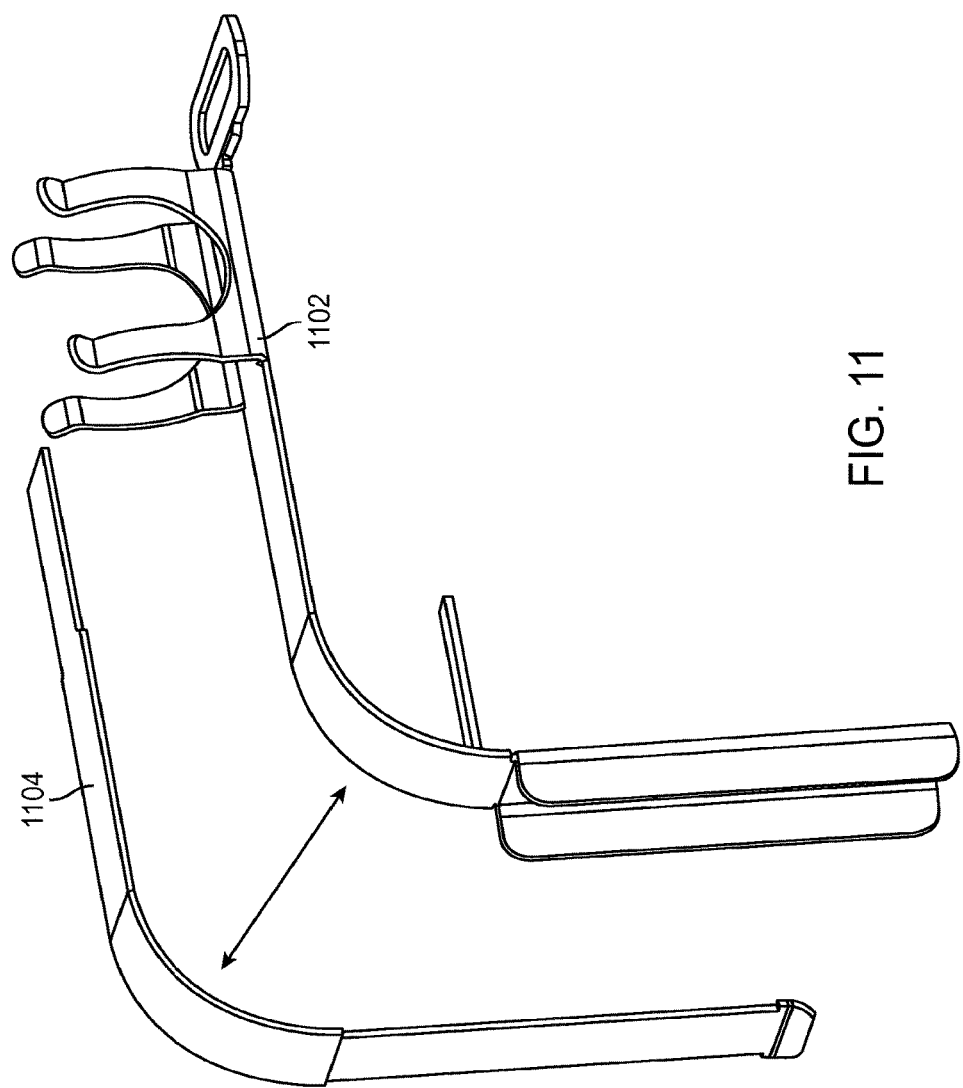
FIG. 11 illustrates an exemplary embodiment of a thermal element disposed between the illumination element and the rear shield.

Another exemplary technique of controlling temperature in the rear shield includes using a laminated rear shield or a backing strip. FIG. 11 illustrates an exemplary embodiment of this concept. The rear shield 1102 may be any of the rear shields disclosed herein. A backing strip 1104 is fabricated from thermally conductive material and is preferably bonded or otherwise laminated to the rear shield 1102. The rear shield 1102 is preferably fabricated from a non-thermally conductive material. Thus, the backing strap 1104 is disposed between the illumination element (not shown) and the rear shield. The backing strip absorbs heat from the illumination element and dissipates the heat with low heat transferring to the rear shield. The backing strip preferably conforms to the contours of the rear shield. In an alternative embodiment, the backing strip may include a first strip of material disposed over a second strip of material. One embodiment of this includes a thin aluminum strip about 0.005" to 0.030" thick, more preferably 0.010" to 0.020" thick, and nominally about 0.015" thick that is bonded to a stainless steel strip. Bonding may be achieved using solder paste in a heated clamp. The laminated configuration provides desired mechanical and thermal properties.

In still another exemplary embodiment, a polymer such as fluorinated ethylene propylene (FEP) may be applied to the rear shield, between the rear shield and the illumination element. The layer of FEP polymer may optically prevent light from reaching the light, thereby preventing it from overheating. The FEP may prevent some or all of the light from reaching the suction tube.

In any of the embodiments described herein, retracting the illumination element proximally may result in the illumination element cantilevering upward and away from tissue in the surgical field due to the force vectors. This is undesirable since the illumination element may obstruct the surgical field, and the light emitted therefrom may not illuminate the surgical field properly. Or the illumination element may fall away from the surgical field. Therefore, in an alternative embodiment, the strap that couples the proximal portion of the rear shield or the proximal portion of the illumination element may be coupled further distally along the rear shield or the illumination element. This changes the force vectors and therefore reduces cantilevering of the illumination element upward and away from the surgical field. In still other embodiments, the proximal portion of the rear shield or illumination element may be extended to a longer length to also reduce the cantilevering. In still other embodiments, a ramp may be placed under the proximal portion of the rear shield or the proximal portion of the illumination element. The ramp is angled to help prevent cantilevering. Also, the strap used in any of the disclosed embodiments are preferably resilient so as to further prevent cantilevering. Rigid straps may be used. The straps may be fabricated from any number of materials such as metals, polymers or other materials known in the art.

Figure 7:
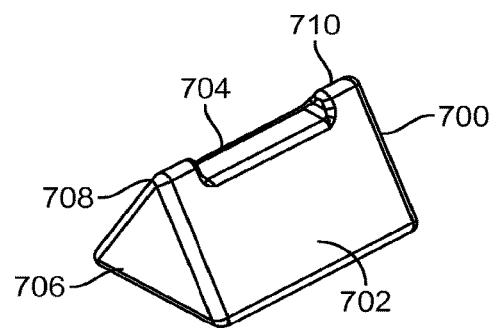
FIG. 7 illustrates an exemplary embodiment of a ramp.

FIG. 7 illustrates an exemplary embodiment of a ramp 700 which is generally a triangular shape having a flat base 706 that can rest against a patient with flat inclined surfaces 702. At the apex 708 of the ramp, a recessed region 704 is formed to accommodate the strap previously described. Shoulders 710 which extend beyond the ramp provide a stop on either side of the recessed region to help hold and prevent unwanted movement of the strap in the recessed region 704. The ramp may be injection molded from a polymer or may be machined from wood, polymer, metal or any other suitable material.

Figure 8:
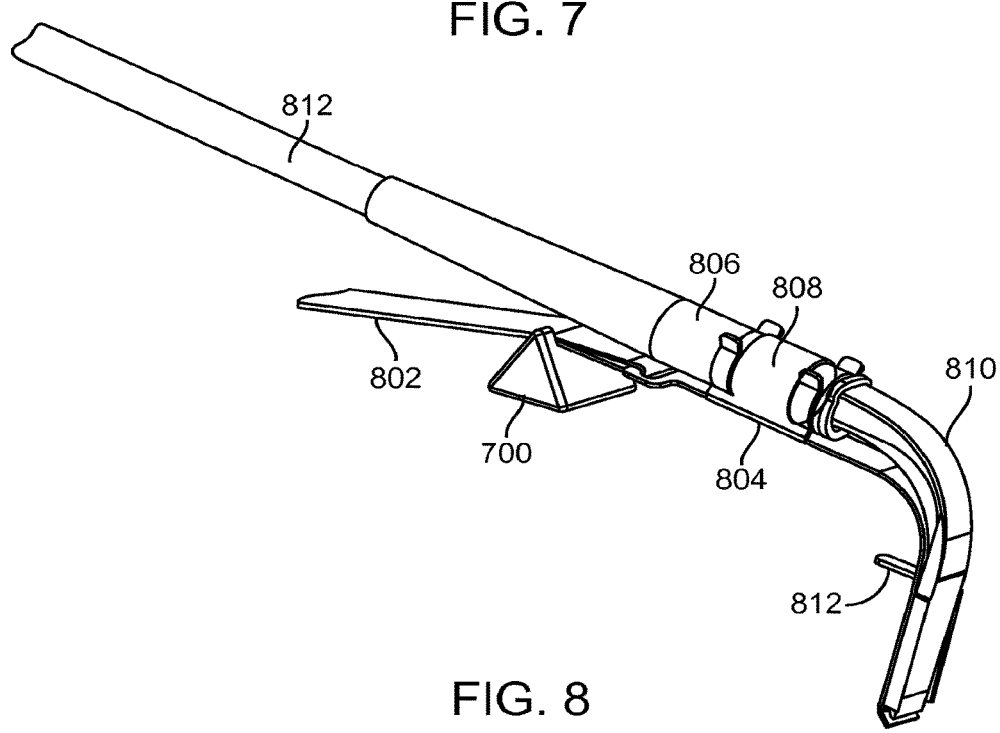
FIG. 8 illustrates use of the ramp in FIG. 7 along with a rear shield.
Figure 9:
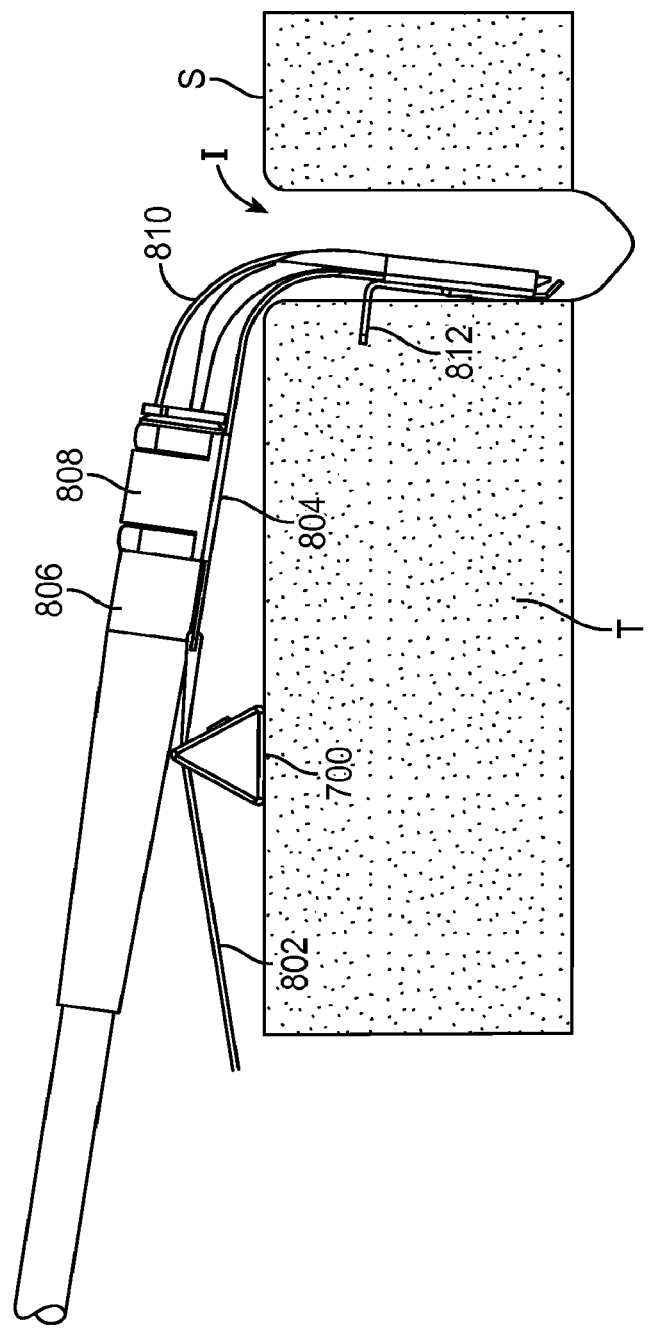
FIG. 9 illustrates the ramp in FIG. 7 used in a surgical field.

FIG. 8 illustrates the ramp 700 coupled to a rear shield 804 which may be any of the rear shield embodiments described in this specification. A tether 802 is coupled to the slot in the rear shield and is disposed on the recessed region of the ramp 700. An illumination element 810 such as an optical waveguide is coupled to the rear shield 804 and a fiber optic cable 812 is coupled to the waveguide. A portion 808 is coupled to the rear shield with the resilient fingers of the rear shield. Portions of the cable 812 may be covered with a polymer 806 or knurled, textured or otherwise have surface modifications to help engagement with the resilient fingers or other portions of the rear shield. The strap 802 can now be retracted to apply tension to the rear shield and the ramp prevents cantilevering (sometimes also referred to as toe-out) of the distal portion of the illumination element. Anchor 812 therefore remains engaged with tissue. FIG. 9 illustrates the rear shield disposed in an incision I of a patient with the ramp 700 sitting on the patient's skin or on a surgical drape (not illustrated). The tissue anchor 812 remains engaged with tissue T while tension is applied to strap 802.

In any of the embodiments disclosed herein, the illumination element, the rear shield, or any other portion of the system may include wings or extensions which are coupled thereto and which extend laterally outward therefrom. These wings may be used provide greater surface area and assist with retraction of tissue, or the wings may form an area that can be pinched between a retractor or other surgical instrument and tissue, thereby further anchoring a portion of the system to the patient.

Additionally, any of the embodiments described herein may also include imaging capability. For example, the illumination element, rear shield, anchor, or any component of the illumination system may be coupled to an imaging element such as a fiber optic cable, an endoscope, a laparoscope, a CCD chip, CMOS or any other imaging element known in the art. Thus, the illumination element provides light for the imaging element, and the imaging element captures an image of the surgical field. A video or one or more images may be produced by the imaging element. Moving the illumination element or the anchor allows illumination of the surgical field to be varied, and moving the imaging element with it also allows different portions of the surgical field to be imaged. In still other embodiments, the anchoring mechanisms described herein may be used to anchor an imaging element to the patient or to adjacent surgical equipment, with or without an illumination element. Thus, the anchoring mechanisms secure an illumination element such as a fiber optic, an endoscope, a laparoscope, a CCD chip, CMOS, or other illumination element and it may be easily adjusted to allow visualization of the surgical field.

Figure 12:
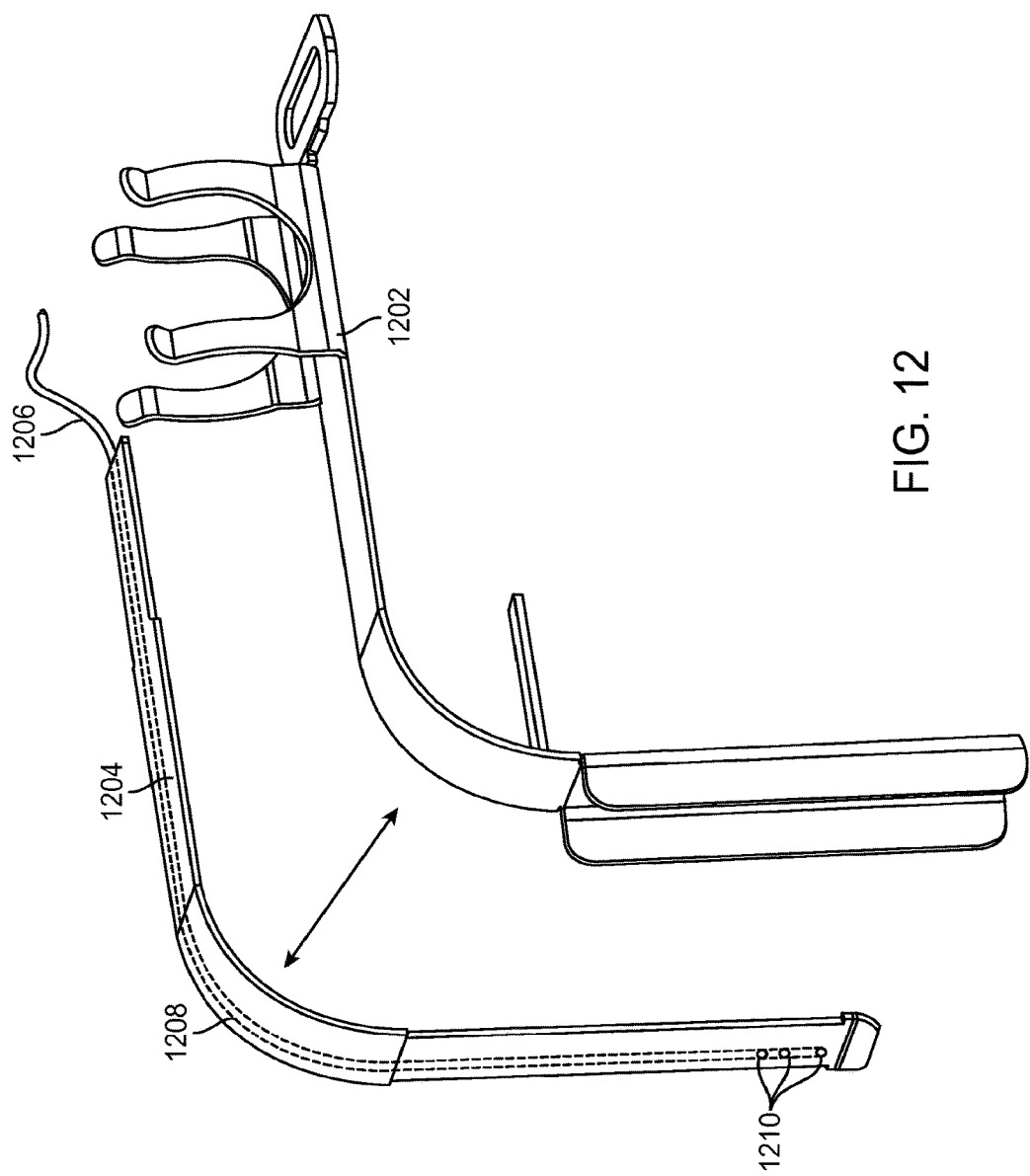
FIG. 12 illustrates an illumination element and rear shield configured to remove smoke or other fumes.

Optionally, any of the embodiments described herein may also be configured to remove smoke or other noxious fumes from the surgical field. FIG. 12 illustrates an exemplary embodiment of such a device which includes a rear shield 1202 and illumination element 1204. The rear shield 1202 may be any of the rear shields disclosed herein and the illumination element 1204 similarly may be any of the illumination elements disclosed herein. In this embodiment, the illumination element 1204 includes a suction element such as a smoke evacuation channel 1208 extending therethrough. Distal apertures 1210 allow smoke or other fumes to be suctioned into the channel 1208 when vacuum is applied and withdrawn from the surgical field. Tubing 1206 allows the channel 1208 to be coupled to an external source of vacuum and the fumes are drawn away through tubing 1206. Thus, the surgical field can be illuminated and fumes can be removed simultaneously. In other embodiments, the channel 1208 may be replaced by a separate suction element such as a tube which is disposed on an outer surface of the illumination element 1204. In still other embodiments, the channel may be disposed in the rear shield, or the separate tube may run alongside of the rear shield. In yet another embodiment, the illumination element with suction channel or separate suction tube may be used alone, without the rear shield, as previously described above. In other embodiments, only a suction element may be employed with the anchors described herein, or the suction may be combined with the illumination element and/or the imaging element. Also in any of these embodiments, the illumination element, suction element, or imaging element may be formed integrally with the anchoring mechanisms so that there is only a single piece device, rather than having several components coupled together.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An illumination system for adjustably positioning an illuminator in a surgical field in a patient, said system comprising:
   an anchor element configured to be releasably coupled with the patient;
   a shield element having a proximal portion and a distal portion, wherein the proximal portion includes a generally planar section and an attachment section configured for attachment to the anchor element, and wherein the distal portion is generally transverse to a plane in which the proximal portion lies;
   an illumination element releasably coupled to the shield element, wherein the shield element is configured to be coupled, uncoupled, and recoupled with the anchor element, thereby allowing repositioning of the illumination element at a plurality of positions in the surgical field without interfering with adjacent surgical instruments, and further permitting adjustment of illumination in the surgical field, wherein the shield element shields the illumination element from direct contact with the surgical field; and
   a non-adhesive tissue engagement element integral with the shield element or configured to be releasably coupled to the shield element, the non-adhesive tissue engagement element extending parallel to the plane in which the proximal portion lies and configured to anchor the shield element to tissue in the surgical field without retracting tissue and without engaging the patient's skin, the non-adhesive tissue engagement element further configured to be fully disposed in the surgical field and below and parallel to the patient's skin.

2. The system of claim 1, wherein the anchor element has a first side configured to be releasably coupled to the patient or the adjacent surgical equipment.

3. The system of claim 2, wherein the first side comprises an adhesive configured to releasably attach the anchor element to the patient or the surgical equipment adjacent thereto.

4. The system of claim 3, wherein the adhesive comprises tape.

5. The system of claim 1, wherein the anchor element comprises hook or loop elements, and wherein the illumination element comprises hook or loop elements for releasably coupling with the hook or loop elements on the anchor element.

6. The system of claim 1, wherein the anchor element comprises a clip or a hook for releasable coupling with the patient or the adjacent surgical equipment.

7. The system of claim 1, wherein the anchor element or the illumination element comprises a magnet for releasably coupling with the other of the anchor element or the illumination element.

8. The system of claim 1, wherein the anchor element comprises one or more hooks for releasably coupling with the illumination element.

9. The system of claim 1, wherein the anchor element forms a c-shaped loop, the c-shaped loop configured to at least partially encircle an incision in the patient.

10. The system of claim 1, further comprising a surgical retractor having a retractor blade, and wherein the anchor element is unattached to the surgical retractor blade.

11. The system of claim 10, wherein the illumination element is configured to be disposed in the surgical field without contacting the surgical retractor.

12. The system of claim 1, wherein the illumination element is a LED, OLED, fiber optic cable or a non-fiber optic optical waveguide.

13. The system of claim 1, wherein the non-adhesive tissue engagement element is configured to anchor the distal end of the shield element to tissue in the surgical field without adhesives.

14. The system of claim 13, wherein the non-adhesive tissue engagement element comprises a hook or a barb.

15. The system of claim 1, further comprising an imaging element coupled to the illumination element or the shield element, the imaging element configured to provide images of the surgical field.

16. The system of claim 1, further comprising a suction element on or in the shield element configured to remove smoke or noxious fumes from the surgical field.

\* \* \* \* \*